United States Patent [19]
Horn et al.

[11] Patent Number: 5,852,206
[45] Date of Patent: Dec. 22, 1998

[54] PROCESS FOR REMOVING RESIDUAL ACIDIC CHLORINE FROM ACYLOXYSILANES

[75] Inventors: Michael Horn; Hartwig Rauleder; Claus-Dietrich Seiler; Jaroslaw Monkiewicz, all of Rheinfelden, Germany

[73] Assignee: Huels Aktiengesellschaft, Marl, Germany

[21] Appl. No.: 980,116

[22] Filed: Nov. 26, 1997

[30] Foreign Application Priority Data

Nov. 27, 1996 [DE] Germany .................... 196 49 023.5

[51] Int. Cl.$^6$ ........................................ C07F 7/08
[52] U.S. Cl. ............................. 556/466; 556/442
[58] Field of Search ....................... 556/466, 442

[56] References Cited

U.S. PATENT DOCUMENTS 5,084,588  1/1992  Ocheltree et al. ............. 556/466

*Primary Examiner*—Paul F. Shaver
*Attorney, Agent, or Firm*—Oblon, Spivak, McClelland, Maier & Neustadt, P.C.

[57] ABSTRACT

A process for removing residual acidic chlorine from acyloxysilanes, comprises virtually quantitatively reacting metal carboxylates with the acidic chlorine present in the acyloxysilane, and the metal chlorides formed being separated off.

19 Claims, 2 Drawing Sheets

PROCESS FOR REMOVING RESIDUAL ACIDIC CHLORINE FROM ACYLOXYSILANES

BACKGROUND OF THE INVENTION

1. Field of the Invention:

The invention relates to a process for removing residual acidic chlorine contents from acyloxysilanes, and to acyloxysilanes which are obtainable by the present process.

2. Discussion of the Background:

Acyloxysilanes have many applications in the chemical industry. They are suitable for example, as cross-linking silicon compounds in the preparation of compositions which are storable in the absence of water and hardenable at room temperature on exposure to moisture. Examples include compounds such as methyl-, ethyl- and propyl-tris (ethanoyloxy)silane.

For silanes of this type, the purity requirements regarding The residual chlorine content in the form of acidic chlorine, have recently increased substantially. Residual chlorine content in acyloxysilanes originates from the incomplete reaction of all of the chlorine of the organochlorosilane starting materials with reagents which introduce the acyloxy group. In the context of the present invention, acidic chlorine means chlorine which is bound to the silicon in the silane, hydrogen chloride, and chlorine present as acyl chloride.

Essentially two procedures are used to prepare acyloxysilanes on an industrial scale. One procedure makes use of the reaction of organochlorosilanes with carboxylic acids to give the corresponding organoacyloxysilanes. This procedure is practiced both batchwise and continuously.

Batchwise preparation requires the presence of an inert solvent and long reaction times to decrease the residual acidic chlorine content to values below 100 ppm (U.S. Pat. Nos. 2,437,073; 2,866,800; 3,974,198; and GB 814,01 1). Continuous reaction of organochlorosilanes with carboxylic acids is disclosed in the publications DE-C 2,801,780; DE-C 3,721,702; EP-A 0,003,317; and U.S. Pat. Nos. 4,332,956; and 4,329,484. When a small excesses of carboxylic acid is used, based on the amounts of organochlorosilane, the acidic chlorine content remains on the orders of up to 50 ppm; only the use of a large excesses of carboxylic acid—on the order of 50%—enables the acidic chlorine content to be decreased to values below 1 ppm, with an unsatisfactory siloxane content being tolerated.

The other procedure for preparing acyloxysilanes on an industrial scale makes use of the reaction of organochlorosilane with carboxylic anhydride to give the corresponding organoacyloxysilanes and acyl chloride. FR-B 1,003,073 describes the batchwise and simultaneous preparation of acyloxysilanes and acyl chlorides by reacting organochlorosilanes with monocarboxylic anhydrides. Unsatisfactory product yields with an undetectable residual chlorine content is obtained after a reaction time of 8 hours.

A continuous method of preparation of acyloxysilanes is disclosed in EP-B 0,509,213. Organochlorosilanes are reacted with carboxylic anhydrides in the presence of specific catalysts to give acyloxysilanes and acyl chlorides. The special procedure enables the acidic chlorine content in the end products to be decreased, for example, from 800 ppm to 3 ppm. However, a reduction of the acidic chlorine content below the limits of detection is only achievable by this procedure with the use of greatly extended reaction times and with the use of considerably higher amounts of carboxylic andydride.

The literature also describes procedures for preparing acyloxysilanes by reacting the corresponding organochlorosilanes with alkali metal carboxylates in the presence of large amounts of inert diluents. These procedures are associated with the production of considerable amounts of salt, the target product having to be removed from the reaction mixture by complex washing processes. These procedures are scarcely industrially applicable, and also do not conform to current economic and ecological requirements (see U.S. Pat. Nos. 2,573,302; 2,537,073; 2,866,800; and DE-C 870, 554 and GB-B 640,834).

SUMMARY OF THE INVENTION

The object of the present invention is to provide a process for removing residual amounts of acidic chlorine from acyloxysilanes which enables the residual acidic chlorine content in the acyloxysilanes to be decreased to values below 2 ppm by weight of chlorine, and furthermore, enables the product to remain essentially free of siloxanes. It was also a particular concern of the present invention to keep the production of solvents and salts as low as possible.

Surprisingly, it has now been found that it is possible to decrease residual acidic chlorine contents in acyloxysilanes to values considerably below 1 ppm by weight in a simple and economical manner, i.e., to essentially remove them, by adding metal carboxylates and separating off the resulting metal chlorides. This does not require significant amounts of solvent, and furthermore, no additional siloxanes are formed in the product.

The objects are achieved by a process for removing residual acidic chlorine from acyioxysilanes, comprising reacting virtually quantitatively the acidic chlorine present in the acyloxysilane by adding metal carboxylates and separating off the metal chlorides formed.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

Figure 1:
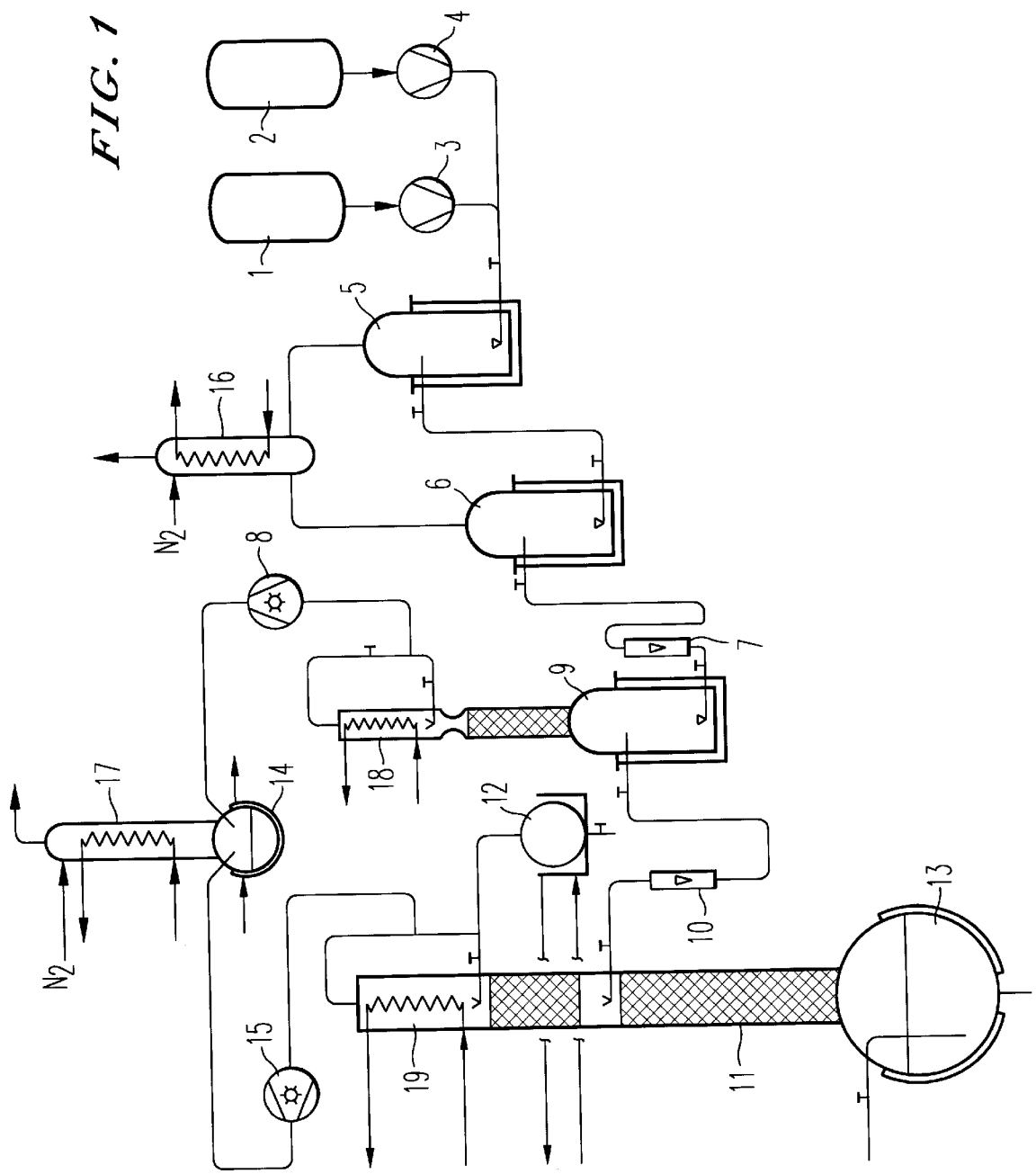
FIG. 1 shows a diagram of a plant for preparing acyloxysilane.

The acyloxysilanes usable as starting materials for the purification process according to the invention correspond to the general formula (I):

$$R^1{}_a R^2{}_b Si(-O-CO-R^3)_{4-a-b} \tag{I}$$

where a is 3, 2 or 1; b is 1 or 0; and $a+b \leq 3$; preferably $a=1$ and $b=0$. $R^1$ and $R^2$ are hydrogen; or saturated or unsaturated hydrocarbon radicals each having 1 to 10 carbon atoms which may possess functional groups, such as halogen, and are not attacked under the specified reaction conditions; and also cyclic saturated or unsaturated hydrocarbon radicals, for example, those having 6 carbon atoms. $R^1$ and $R^2$ are identical or different in the present formula. $R^3$, in the abovementioned formula, represents hydrogen, methyl, ethyl or propyl.

For example, the following acyloxysilanes, which may be prepared by the processes described at the outset and generally have an acidic chlorine content of 2 ppm by weight or more, can be used in the process according to the invention: vinyltris(ethanoyloxy)silane, ethyltris(ethanoyloxy)silane, methyltris(ethanyloxy)silane, propyltris(ethanoyloxy)silane, 2-chloroethyl-methylbis(ethanoyloxy)silane, ethyl tris(propanoyloxy)silane , phenyltris(ethanoyloxy)silane.

For the processes according to the invention, generally any of the known metal carboxylates of the elements of the Periodic Table which form salt-like metal chlorides in a suitable manner; some preferred examples which may be mentioned are as follows: sodium format, sodium acetate, sodium propionate, sodium butyrate, potassium acetate, magnesium acetate, calcium acetate, barium acetate, zinc acetate. In particular, the metal carboxylates used are carboxylates of the alkali metal elements and/or alkaline earth metal elements. Particular preference is given to the carboxylates of sodium.

In the invention, the metal carboxylates are used dissolved in the carboxylic acid corresponding to the metal carboxylate. The carboxylates are preferably used in amounts such that there is no excess over the stoichiometrically necessary amount, based on the acidic chlorine content in the substrate to be treated.

Complete removal of the acidic chlorine from organoacyloxysilanes can be achieved by a single addition of a corresponding amount of a metal carboxylate. Alternatively, only approximately 70–80% of the amount of carboxylate stoichiometrically required for the complete removal of the acidic chlorine from the substrate is added, the mixture is allowed to react, and the residual acidic chlorine content is again determined, and depending on the acidic chlorine content remaining in the substrate, 70–80% of the stoichiometrically required amount of carboxylate is again added. In this manner, the desired residual acid chlorine content in the substrate can be approached stepwise without the product being exposed during the work-up by distillation to the risk of decomposition due to an excess of carboxylate.

In a suitable manner, in the process according to the invention, the residual acidic chlorine is reacted at a temperature of 0° to 200° C., preferably at 0° to 130° C., particularly preferably at 20° to 80° C. The reaction maybe carried out either at reduced pressure, for example above 400 mbar absolute, or at atmospheric or elevated pressure, for example up to 2 bar absolute. To enhance and accelerate the reaction, the reaction may further be performed with stirring. Depending on the properties of the substrate to be treated, the reaction temperature should, if possible, be selected so that the reaction time and the solubility of the resulting metal salts in the substrate are minimized.

When the residual acidic chlorine content has reached its target value or after its complete removal, metal salts which have formed arc removed. The metal chlorides which are formed in the reaction may be separated off in various ways. Filtration is preferably employed in those cases where, in a product otherwise conforming to specifications, a low content of hydrolyzable chlorine, i.e. acidic chlorine, is to be further reduced or lowered below the detection limit. The metal salts may be separated off from the product by centrifugation.

Distillation, for example in the context of working up the organoacyloxysilane crude products to give the end product, which is customarily performed following the metal carboxylate treatment, may also be employed. This method is preferably used when, to increase the capacity of the plant, the removal of residual acidic chlorine content is terminated in an early stage. In addition to the increase in capacity, a further beneficial effect which results is a reduced formation of unwanted siloxanes. This procedure can be employed for preparing organoacyioxysilanes in both a continuous and a batchwise manner. In the batchwise preparation of organoacyloxysilanes, the metal chlorides generally remain in the distillation bottom phase and can be removed from the system with the latter in a known manner.

In a continuously operating plant for preparing organoacyloxysilanes, a constant acidic chlorine content is established in the end product which is customarily taken off continuously from the tower still pot. In accordance with this acidic chlorine content, a defined generally stoichiometric amount of metal carboxylate, for example dissolved in the carboxylic acid corresponding to the metal carboxylate, may be added to the end product situated in the take-off still pot, and the metal chloride which precipitates out can be removed by filtration after removal of the product, if appropriate after cooling the same. If small amounts of carboxylic acids in the end product interfere, these can be removed by distillation. The term continuous means that the various steps of the process are carried out simultaneously.

However, subsequent work-up by distillation of the suspension comprising the product and the metal chloride is, under certain circumstances, the preferred method to be used to separate off the metal chlorides. Particularly effective removal of the precipitated metal chlorides from the product may also be arranged by using a separator or a centrifuge.

In the present invention, organoacyloxysilane freed from residual chlorine content means those products whose acidic chlorine content is generally less than 2 ppm by weight, in particular less than 1 ppm by weight, preferably less than 0.5 ppm by weight of acidic chlorine, particularly preferably less than or equal to 0.1 ppm by weight.

The process according to the invention for removing acidic chlorine in acyloxysilanes can be applied in an outstanding manner to all acyloxysilanes whose acidic chlorine content is to be decreased, in particular to values below 1 ppm by weight.

Having generally described this invention, a further understanding can be obtained by reference to certain specific examples which are provided herein for purposes of illustration only and are not intended to be limiting unless otherwise specified.

EXAMPLES

Comparison Example A

The reaction is carried out in a conventional laboratory apparatus consisting of a multineck flask, an agitator, a dropping funnel, a thermometer and a reflux condenser. 315 g (5.25 mol) of ethanoic acid are added in the course of 2.5 hours to an introduced mixture of 224.3 g (1.5 mol) of methyltrichlorosilane and 100 ml of hexane. Addition is performed while the flask contents are refluxing.

After completion of the addition of ethanoic acid, the mixture is refluxed for a further 3.5 hours. The hexane is then removed at atmospheric pressure by distillation until the bottom temperature has reached 120° C. The refluxing is then continued for a further hour at a pressure of 60 mmHg. Determination of the acidic chlorine contents in the flask product gives a value of 97 ppm. After removal of excess ethanoic acid by distillation, a product having the composition shown below is produced:

methyltris(ethanoyloxy)silane 93.1% by weight
dimethyltetrakis(ethanoyloxy)silane 6.2% by weight high boilers 0.7% by weight
acidic chlorine 83 ppm by weight

Example 1

The procedure described in Comparison Example A is repeated, but the addition time is halved and the total reaction time (including post-reaction time) is restricted to 3.26 hours. The flask contents are examined for their acidic chlorine content. An acidic chlorine content of 420 ppm by weight is determined, which corresponds to a total acidic chlorine amount of 202 mg for flask contents of 481 g.

5.832 g of a solution of sodium ethanoate in ethanoic acid (8.0 g of sodium ethanoate in 92 g of ethanoic acid) are then added to the flask contents cooled to 50° C. and the mixture is allowed to react for 5 minutes with vigorous stirring. After cooling the flask contents to room temperature, the precipitated sodium chloride is separated off. In the liquid, the acidic chlorine content is determined to be below 0.1 ppm by weight. After removal of excess ethanoic acid by distillation, a product having the following composition is produced:

methyltris(ethanoyloxy)silane 96.1% by weight
dimethyltetrakis(ethanovloxy)silane 3.1% by weight
high boilers 0.5% by weight
ethanoic acid 0.3% by weight
acidic chlorine <0.1 ppm by weight

Example 2

A 4500 mm-long tube made of acid-resistant material having an internal diameter of 120 mm packed with Raschig n rngs is used as a tower. The top end of the tower tube is attached to a reflux condenser, which is operated with CaCl$_2$ brine at −32° C. At the bottom end of the tower tube there is a flask which serves as collection vessel for the synthesis product. Using a pump, liquid is continuously taken off from the collection vessel at a rate such that the liquid level remains unchanged. The liquid pumped off is collected in a receiving vessel which can be heated and which is fitted with an agitator.

800 ml (992 g, 6.067 mol) of ethyltrichlorosilane are fed per hour into the center of the tower tube with the help of a metering pump. Approximately 500 mm above the collection vessel for the synthesis product, 1100 ml (1154 g, 19.23 mol) of ethanoic acid are added to the tower tube per hour by a second metering pump. The tower inlet temperature of the ethanoic acid is above 100° C. A pressure of 120–130 mmHg is maintained in the tower. After an inflow time of approximately 10 hours, a product is produced and collected in the collection vessel below the tower end, which has an acidic chlorine content of approximately 43 ppm by weight.

From this time point, the product produced in the collection vessel is transferred to a downstream receiving vessel, with the liquid level kept constant, and is there admixed with a solution of sodium ethanoate in ethanoic acid with stirring at a temperature of 85° C., which accelerates the conversion of the hydrolyzable chlorine to sodium chloride. The metered addition of the sodium ethanoate/ethanoic acid solution is controlled by analytical monitoring in such a way that a hydrolyzable chlorine content present in the product is <0.1 ppm by weight. In the present case this value is achieved by feeding to the receiving vessel, in one or more portions, 3.52 g per hour of a sodium ethanoate/ethanoic acid solution which contains 4.0 g of sodium ethanoate in 96 g of ethanol.

The suspension of product and sodium chloride which forms in the receiving vessel is passed through a filter and the solid sodium chloride portion is thus removed. The filtrate produced has the following composition:

ethyltris(ethanoyl)silane 93.4% by weight
diethyltetrakis(ethanoyloxy)siloxane 4.8% by weight
ethanoic acid 1.8% by weight
chlorine <0.1 ppm by weight

Example 3

The procedure described in Example 2 is repeated. In the center of the tower tube, an amount of 1200 ml (1488 g, 9.10 mol) of ethyltrichlorosilane is fed in per hour, and in the bottom part of the tower 1650 ml (1731 g, 28.85 mol) of ethanoic acid is fed in per hour.

After an inflow time of 10 hours, a product is produced and collected in the collection vessel below the tower end, which has a constant acidic chlorine content of approximately 95 ppm by weight. The after treatment described in Example 2 with 11.635 g per hour of a solution of 4.0 g of sodium ethanoate in 96.0 g of ethanoic acid causes a filtrate to be produced which has the following composition:

ethyltn rs(ethanoyl)silane 95.9% by weight
diethyltetrak -is(ethanoyloxy)siloxane 1.8% by weight
ethanoic acid 2.3% by weight
acidic chlorine <0.1 ppm by weight

Comparison Example B 300 g (2 mol) of methyltrichlorosilane and 990 g (6.7 mol) of ethanoic anhydride, admixed with 40 mg of N,N-dimethylethanamide are heated in a conventional laboratory distillation unit. At the top of the tower distillation unit, ethanoyl chloride is taken off over a period of 7 hours, until the reflux greatly diminishes. Residual ethanoyl chloride and excess ethanoic anhydride are removed under reduced pressure. A product which comprises 91.1% by weight of methyltris(ethanoyloxy)silane having an acidic chlorine content of 84 ppm by weight remains in the still pot.

Example 4

Comparison Example B is repeated. At the tower top, ethanoyl chloride is taken off more intensively over a period of 4 hours. After removing excess ethanoic anhydride under reduced pressure, a bottom product is present which comprises 95.7% by weight of methyltris(ethanoyloxy)silane having a residual acidic chlorine content of 210 ppm by weight.

The product (432 g) transferred from the distillation still pot to a flask equipped with an agitator device is admixed at a temperature of 60° C. with 5.22 g of a solution of 4.0 g of sodium ethanoate in 96.0 g of ethanoic acid. After a reaction time of 5 minutes, the sodium chloride formed is allowed to settle and the supemate liquid is decanted. The supernate comprises 95.1% by weight of methyltris(ethanoyloxy) silane, 1.1% by weight of ethanoic acid and has an acidic chlorine content of less than 0.1 ppm by weight.

Comparison Example C

FIG. 1 shows the diagram of a plant for preparing acyloxysilanes. Ethyltrichlorosilane is charged into the receiving vessel 1, and ethanoic anhydride into the receiver 2. By means of the metering pumps 3 and 4, 157 g (0.96 ml) of ethyltrichlorosilane per hour and 352 g (3.46 mol) of ethanoic anhydride per hour, admixed with 51 mg of triethylamine, are fed into the lower part of the reactor 5

(volume =1 liter), in which the starting materials are heated to 60° C. After passing through the reactor 5, the reaction mixture passes via condenser 16 into the reactor 6 (volume =1 liter) in which it is kept at 60° C. and from which it is then passed via the rotor meter 7 at a rate of approximately 510 g per hour into the distillation reactor 9 (volume =1 liter). In this reactor, the reaction mixture is heated to 90° C. and the previously formed and still forming ethanoyl chloride is distilled off from the reaction mixture at a pressure of 50 to 60 mbar (vacuum pump 8) and led off via the condenser 18 to the cooled receiver 14. The amount of ethanoyl chloride collected in the receiver 14 per hour is approximately 216 g (2.76 mol).

Using the rotor meter 10, the product taken off in the upper part of the distillation reactor 9 is applied to the center inlet of the distillation tower 11, which consists of a 1.60 m-long glass tube having a diameter of 5 cm and is packed with saddle bodies 6 mm in diameter. A cooling liquid (−27° C.) runs through the condenser 19 at the top of the tower and the distillate receiver 12. The lower end of the tower forms a 4-l jacketed flask 13, heated by a thermostat (circulation temperature about 125° C.). At an internal tower pressure of 5 to 7 mbar and a temperature of approximately 110° C. in the tower still pot 13, the crude product fed in is worked up. From the jacketed flask 13 half filled with liquid, ethyltris (ethanoyloxy)silane is constantly taken off in an amount such that the liquid level in the flask 13 remains unchanged. In the upper part of the tower, excess ethanoic anhydride distills off, and is collected in the distillate receiver 12. At the top of the tower, via the condenser 19, and the vacuum pump 15, the residual ethanoyl chloride is distilled off into the receiver 14 fitted with the condenser 17.

The product taken off from the jacketed flask 13 has the following composition:

ethyltris(ethanoyloxy)silane 97.2% by weight siloxanes 1.7% by weight ethanoic anhydride 1.1% by weight acidic chlorine 3 ppm by weight Comparison Example D The procedure described in Comparison Example C is repeated with the following changes:

Instead of 157 g (0.96 mol) of ethyltrichlorosilane and 352 g (3.46 mol) of ethanoic anhydride, 235.5 g (1.44 mol) of ethyltrichlorosilane and 528 g (5.19 mol) of ethanoic anhydride are admixed with 76 mg of triethylamine, and fed in per hour.

The product taken off from the jacketed flask 13, approximately 230 g per hour, has the following composition:

ethyltris(ethanoyloxy)silanc approx. 97.7% by weight siloxanes approx. 1.2% by weight ethanoic anhydride approx. 1.1% by weight acidic chlorine approx. 35 ppm by weight Example 5

Figure 2:
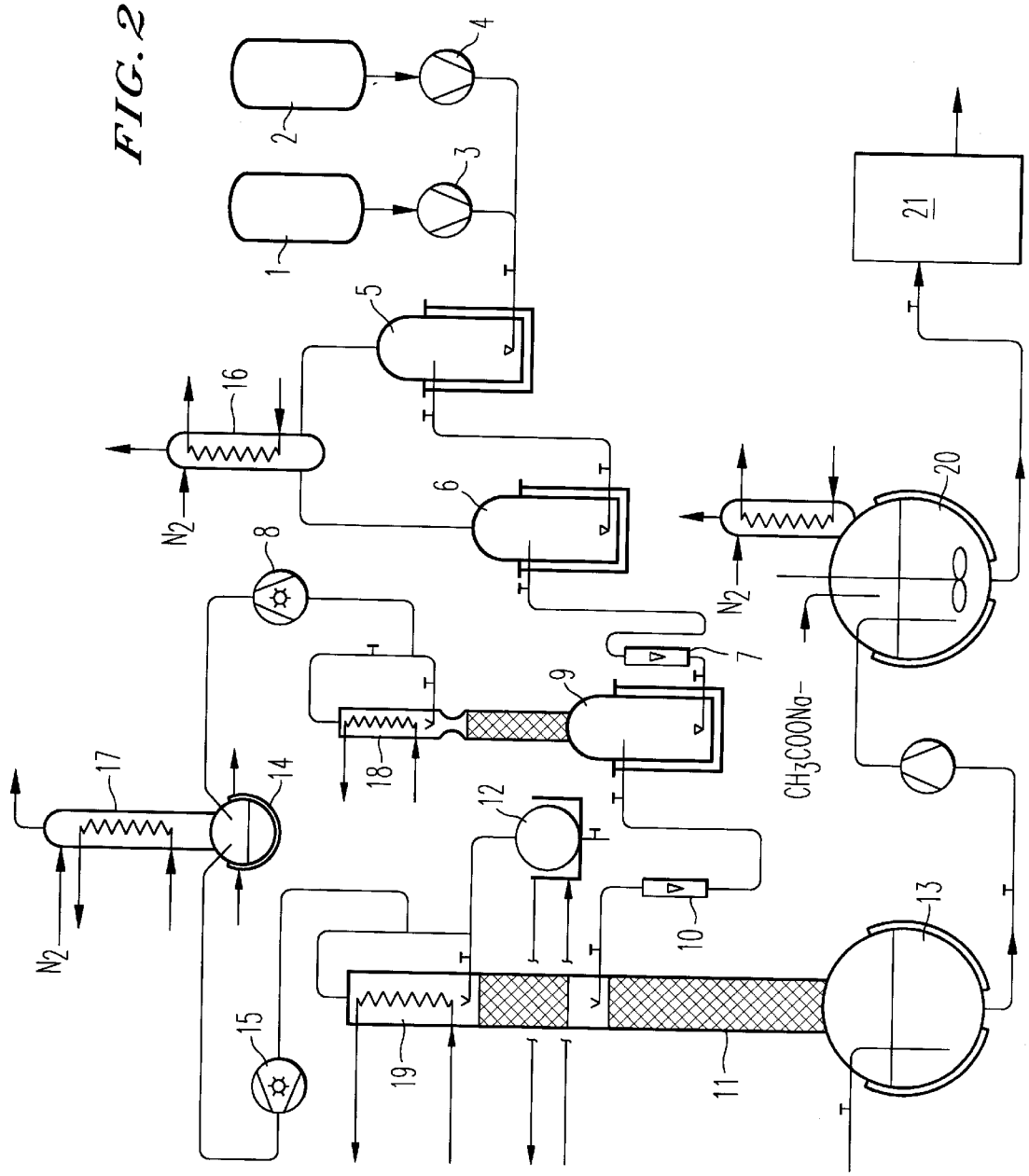
FIG. 2 shows a diagram of a plant for preparing acyloxysilane which includes a receiving flask.

The procedure described in Comparison Example D is repeated, with the following change:

The apparatus shown in FIG. 1 is supplemented with a receiver flask 20, which is equipped with an upstream feed device, jacket, agitator device, mounted condenser, thermometer and bottom outlet port, cf. FIG. 2. A product mixture of constant composition, whose acidic chlorine content is 41 ppm by weight, is taken off from the tower still pot 13 and transferred to the receiver flask 20 which is heated to 90° C. by a heating circuit. The amount of product constantly taken off from the tower still pot 13 is approximately 230 g per hour.

In the course of one hour, an amount of 0.266 g of a solution of 8.0 g of sodium methoxide in 92.0 g of ethanoic acid is added to the receiver flask 20. The suspension of sodium chloride and product forming in the receiver flask is cooled and passed through a separator 21, then, if appropriate, further through a fine filter. The product freed from sodium chloride has the following composition:

ethyltris(ethanoyloxy)silane 97.6% by weight siloxanes 1.1% by weight ethanoic anhydride 1.2% by weight ethanoic acid 0.1% by weight acidic chlorine approx. 0.1 ppm by weight Obviously, additional modifications and variations of the present invention are possible in light of the above teachings. It is therefore to be understood that within the scope of the appended claims, the invention may be practiced othenvise than as specifically described herein.

The priority document of the present application, German Patent Application No. 196 49 023.5 filed on Nov. 27, 1996 is hereby incorporated by reference.

What is claimed as new and is desired to be secured by Letters Patent of the United States is:

1. A process for removing residual acidic chlorine from acyloxysilanes, comprising:

reacting a metal carboxylate with a composition comprising an acyloxysilane and acidic chlorine, to form a metal chloride.

2. The process of claim 1, further comprising separating off said metal chloride.

3. The process of claim 1, wherein an acyl group of said metal carboxvlate is the same an acyl c group of said acyloxysilane.

4. The process of claim 1, further comprising dissolving said metal carboxylate in a solvent, prior to said reacting.

5. The process of claim 4, wherein said solvent is the corresponding carboxylic acid of said metal carboxylate.

6. The process of claim 1, wherein an amount of said metal carboxylate reacted is at most stoichiometrically equivalent to an amount of said acidic chlorine in said composition, for the formation of said metal chloride.

7. The process of claim 1, wherein said metal carboxylate is a carboxylate of at least one alkali metal, at least one alkaline earth metal, or a mixture thereof.

8. The process of claim 1, wherein said reacting is carried out at a temperature of 0–200° C.

9. The process of claim 2, wherein said separating off of said metal chloride is carried out by filtration.

10. The process of claim 1, wherein an amount of said acidic chlorine in said composition prior to said reacting is at least 2 ppm.

11. The process of claim 1, wherein an amount of said acidic chlorine in said composition after said reacting is less than 2 ppm.

12. The process of claim 1, wherein an amount of said acidic chlorine in said composition after said reacting is at most 1 ppm.

13. The process of claim 1, wherein an amount of said acidic chlorine in said composition after said reacting is at most 0.1 ppm.

14. The process of claim 2, further comprising again reacting a metal carboxylate with said composition, to form more metal chloride.

15. The process of claim 1, further comprising:

dissolving said metal carboxylate in a solvent, prior to said reacting; and separating off said metal chloride, after said reacting;

wherein said solvent is the corresponding carboxylic acid of said metal carboxylate, an acyl group of said metal carboxylate is the same an acyl group of said acyloxysilane, said metal carboxylate is a carboxylate of at least one alkali metal, at least one alkaline earth metal, or a mixture thereof, said reacting is carried out at a temperature of 0°–200° C., an amount of said acidic chlorine in said composition prior to said reacting is at least 2 ppm, and an amount of said acidic chlorine in said composition after said reacting is at most 1 ppm.

16. The process of claim 2, wherein said reacting and said separating are carried out simultaneously.

17. A process for producing acyloxysilane, comprising:

reacting an organochlorosilane with a carboxylic acid or a carboxylic anhydride, to form a composition comprising an acyloxysilane and acidic chlorine;

reacting a metal carboxylate with said composition, to form a metal chloride; and separating off said metal chloride from said composition.

18. The process of claim 17, wherein said reacting said organochlorosilane with said carboxylic acid or said carboxylic anhydride, said reacting said metal carboxylate with said composition, and separating off, are all carried out simultaneously.

19. In a process for producing acyloxysilane, including the step of reacting an organochlorosilane with a carboxylic acid or a carboxylic anhydride to form a composition comprising said acyloxysilane and acidic chlorine, the improvement comprising further reacting a metal carboxylate with said composition to reduce the amount of said acidic chlorine present in said composition.

* * * * *